United States Patent
Oskin

(10) Patent No.: US 8,628,311 B2
(45) Date of Patent: Jan. 14, 2014

(54) THERMAL ABLATION SYSTEM WITH DISPENSABLE THERAPEUTIC AGENT

(75) Inventor: Christopher Oskin, Grafton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1067 days.

(21) Appl. No.: 12/206,315

(22) Filed: Sep. 8, 2008

(65) Prior Publication Data

US 2009/0069796 A1 Mar. 12, 2009

Related U.S. Application Data

(60) Provisional application No. 60/971,372, filed on Sep. 11, 2007.

(51) Int. Cl.
*F04B 43/08* (2006.01)

(52) U.S. Cl.
USPC .............................. 417/477.2; 606/27; 606/41

(58) Field of Classification Search
CPC ..................................................... F94B 43/08
USPC ........... 417/477.2; 604/28–30; 606/27, 34, 41
See application file for complete search history.

(56) References Cited

U.S. PATENT DOCUMENTS

| | | | |
|---|---|---|---|
| 5,630,799 A | | 5/1997 | Beiser et al. |
| 5,891,094 A | * | 4/1999 | Masterson et al. ............. 604/113 |
| 6,139,571 A | * | 10/2000 | Fuller et al. ................... 607/105 |
| 6,375,653 B1 | | 4/2002 | Desai |
| 2003/0183226 A1 | * | 10/2003 | Brand et al. ............. 128/200.23 |
| 2004/0267340 A1 | | 12/2004 | Cioanta et al. |
| 2005/0209658 A1 | * | 9/2005 | Machold et al. ................. 607/96 |
| 2005/0235733 A1 | | 10/2005 | Holst et al. |
| 2006/0188407 A1 | * | 8/2006 | Gable et al. .................... 422/100 |
| 2006/0189858 A1 | * | 8/2006 | Sterling et al. ................. 600/310 |
| 2006/0287697 A1 | * | 12/2006 | Lennox ............................ 607/96 |
| 2007/0078370 A1 | | 4/2007 | Shener et al. |
| 2007/0161978 A1 | * | 7/2007 | Fedenia et al. ................... 606/34 |
| 2007/0179436 A1 | * | 8/2007 | Braig et al. ...................... 604/66 |
| 2008/0077073 A1 | * | 3/2008 | Keenan et al. ................... 604/19 |
| 2008/0097563 A1 | * | 4/2008 | Petrie et al. .................... 607/105 |
| 2009/0012450 A1 | * | 1/2009 | Shah et al. ....................... 604/29 |
| 2010/0086420 A1 | * | 4/2010 | Del Pozo Polidoro et al. ............................. 417/474 |
| 2010/0196169 A1 | * | 8/2010 | Krohn ............................. 417/62 |

FOREIGN PATENT DOCUMENTS

| | | |
|---|---|---|
| JP | 2003-284769 | 10/2003 |
| JP | 2005-514085 | 5/2005 |

* cited by examiner

*Primary Examiner* — Nicholas Lucchesi
*Assistant Examiner* — Gerald Landry, II
(74) *Attorney, Agent, or Firm* — Fay Kaplun & Marcin, LLP

(57) ABSTRACT

A cassette for a heated fluid ablation system, comprises a fluid supply lumen receiving an ablation fluid from an external fluid source and a fluid chamber containing a therapeutic agent in combination with an impeller pumping the ablation fluid out of the cassette via to a fluid delivery lumen when the cassette is in a first configuration and pumping the therapeutic agent out of the cassette via the fluid delivery lumen when the cassette is in a second configuration.

16 Claims, 15 Drawing Sheets

Open-Loop (Priming, Cooling)

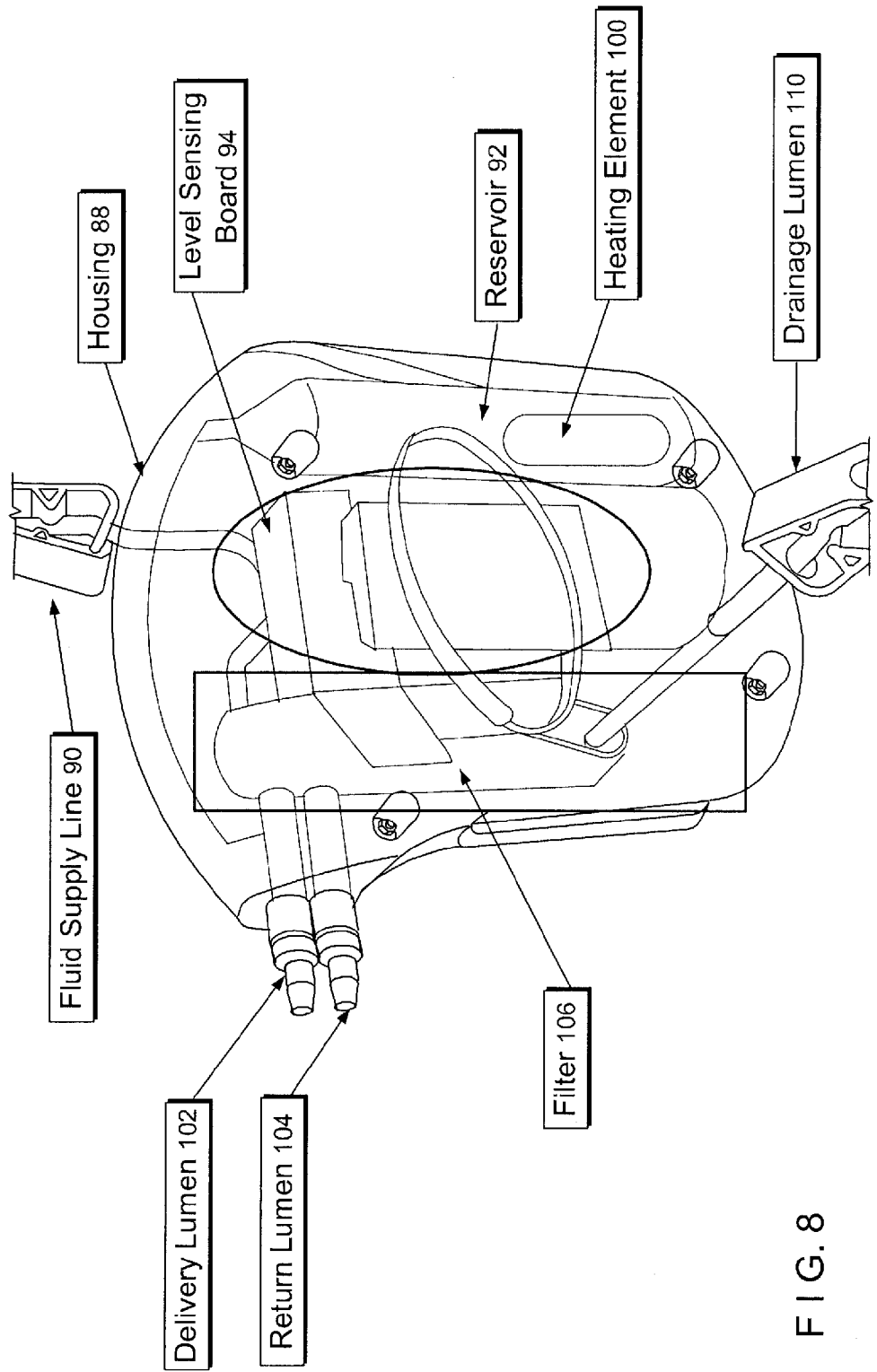
F I G. 8

F I G. 11. Open-Loop (Priming, Cooling)

FIG. 12. Closed-Loop (Heating, Ablation, Pharmaceutical Delivery)

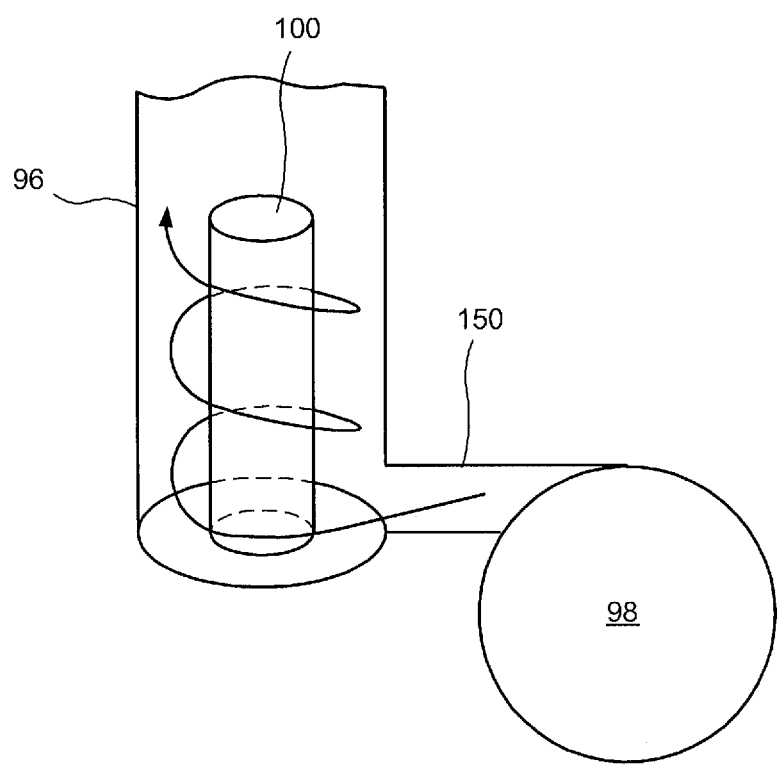
F I G. 13

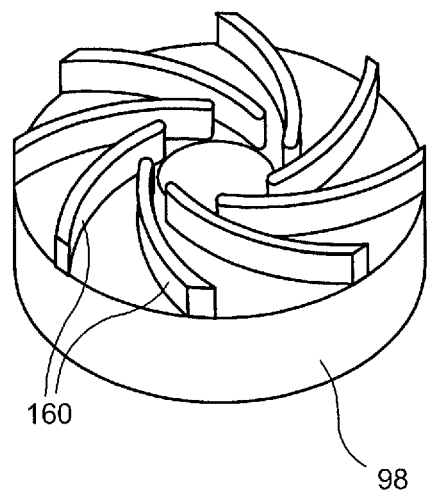
F I G. 14
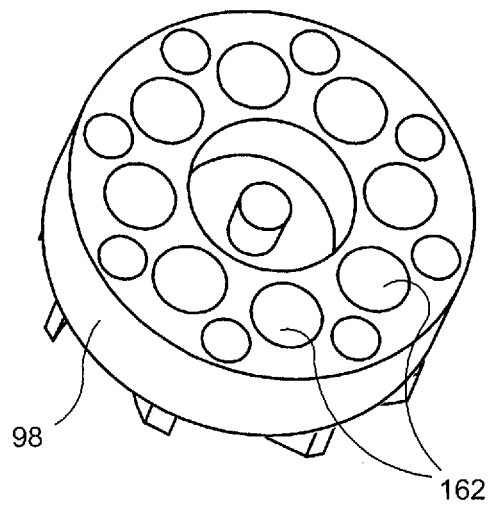
F I G. 15

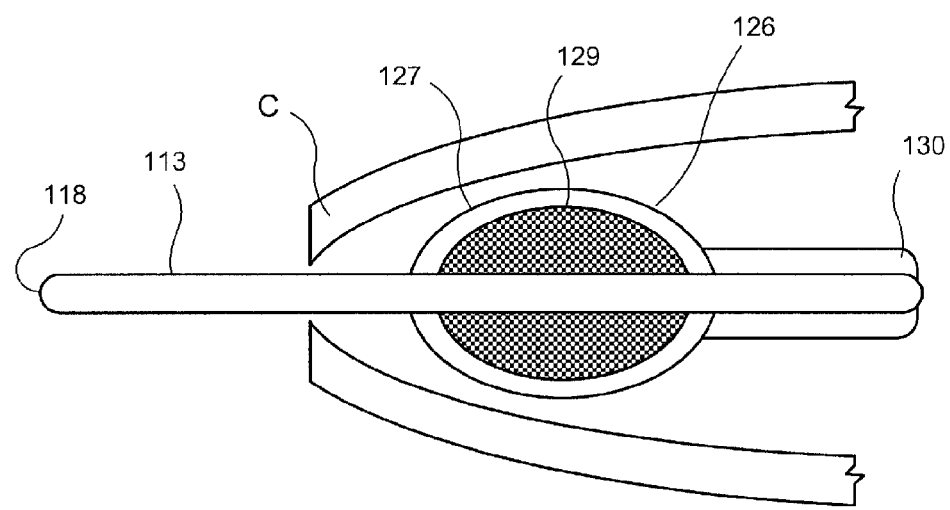
F I G. 16

THERMAL ABLATION SYSTEM WITH DISPENSABLE THERAPEUTIC AGENT

PRIORITY CLAIM

This application claims the priority to the U.S. Provisional Application Ser. No. 60/971,372, entitled "Thermal Ablation System with Dispensable Therapeutic Agent," filed Sep. 11, 2007. The specification of the above-identified application is incorporated herewith by reference.

BACKGROUND

Although hysterectomy is generally an effective treatment for menorrhagia, less invasive procedures are often preferable as they reduce side effects, hospital stays and procedural and post-operative discomfort.

Less invasive procedures treat affected areas of the uterus employing electrical energy (e.g., RF energy), heat (e.g., laser) or cryogenic treatment. However, these procedures typically rely on direct visualization of the uterus by an experienced operator to ensure that the energy is applied to the affected areas of the uterine lining. Alternatively, the entire lining of the uterus may be treated by conduction uterine ablation, i.e., circulation of a heated fluid through the uterus or within a balloon inserted into the uterus.

SUMMARY OF THE INVENTION

The present invention relates to a cassette for a heated fluid ablation system, comprising a fluid supply lumen receiving an ablation fluid from an external fluid source and a fluid chamber containing a therapeutic agent in combination with an impeller pumping the ablation fluid out of the cassette via to a fluid delivery lumen when the cassette is in a first configuration and pumping the therapeutic agent out of the cassette via the fluid delivery lumen when the cassette is in a second configuration.

BRIEF DESCRIPTION OF DRAWINGS

FIG. 8 shows an outer view of an exemplary embodiment of a cassette of a thermal ablation system according to the present invention;

FIG. 13 shows an exemplary embodiment of fluid flow through a heating chamber in a cassette according to the present invention;

FIG. 14 shows an exemplary embodiment of an impeller of a thermal ablation system according to the present invention;

FIG. 15 shows an exemplary embodiment of an impeller of a thermal ablation system according to the present invention; and FIG. 16 shows an exemplary embodiment of a cervical seal of a thermal ablation system according to the present invention.

DETAILED DESCRIPTION

Figure 1:
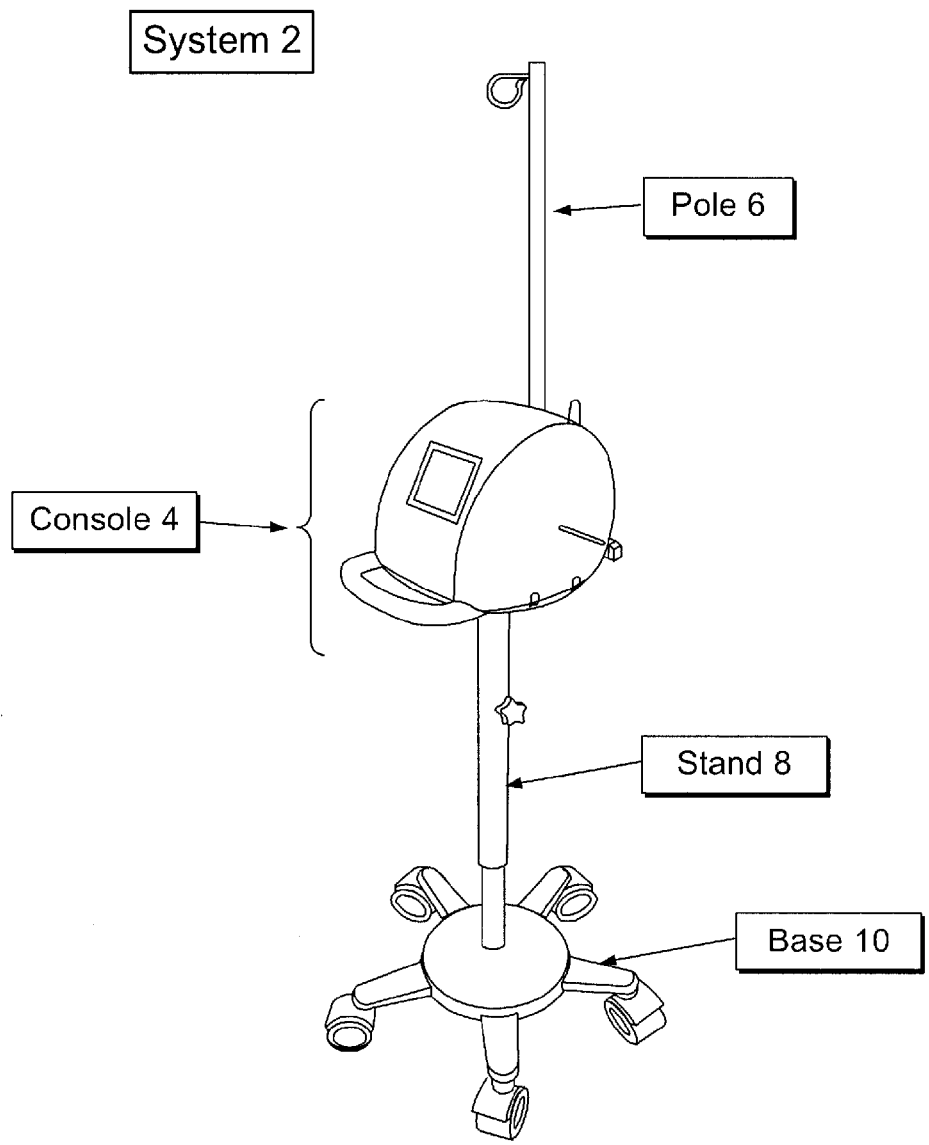
FIG. 1 shows an exemplary embodiment of a thermal ablation system according to the present invention.

The present invention may be further understood with reference to the following description and to the appended drawings, wherein like elements are referred to with the same reference numerals. The present invention relates to systems, methods and apparatus for applying one or more therapeutic agents to tissue, e.g., tissue lining an inner surface of a hollow organ which has been subjected to ablative energy. In one exemplary embodiment, the present invention relates to devices for ablating the endometrial lining using a first fluid (e.g., heated saline) and applying a therapeutic agent to the remaining exposed surface uterine tissue after the ablation. While the exemplary embodiments will be described with reference to applying the therapeutic agent after a tissue ablation procedure, those of skill in the art will understand that the present invention, or components thereof, may be utilized in prostate treatment (microwave or cyroablation) systems, irrigation systems or other procedures which would benefit from applying a therapeutic agent or other fluid, gel, etc. to a tissue prior to, during and/or after a surgical procedure. Those skilled in the art will understand that the term "therapeutic agent" as used throughout the specification, encompasses any nutritive, cleansing, pharmaceutic fluid, gel, etc. which provides a therapeutic effect. Thus, any of saline, water, blood products, nutritive solutions, drugs or combinations of any of these may be employed as a therapeutic agent as that term is used herein.

FIG. 1 shows an exemplary embodiment of a thermal ablation system 2 according to the present invention. Generally, the system 2 includes a console 4 having a pole 6 extending from an upper portion thereof and a stand 8 coupled to a lower portion thereof. The pole 6 preferably extends to a predetermined height above the console 4 so that an intravenous (IV) bag (not shown) hung therefrom will supply fluid to the console 4 at a desired pressure. The IV bag contains fluid (e.g., saline) that will be heated and circulated through the uterus to ablate the endometrial lining. During the ablation procedure, an operator (e.g., physician, nurse, etc.) may be required to substitute the IV bag for IV bags with other fluids depending on stage of the ablation procedure. The IV bags for any fluids required during the procedure may be concurrently attached to the pole 6 with the height of the pole 6 determining the pressure at which these fluids will be supplied to the console 4.

A height of the console 4 relative to the floor is preferably variable using a height-adjusting mechanism between the stand 8 and the console 4 to control a pressure of fluid reaching the treatment site as will be described below. The height-adjusting mechanism may be a pneumatic lift, a frictional lock, etc., allowing the operator to manually adjust of the height of the console 4. In another exemplary embodiment, the height-adjusting mechanism may comprise an automated height adjustment mechanism controlled by user actuation or automatically by electronic circuitry (e.g., in the console 4) based on sensor data, etc.

In the exemplary embodiment, the stand 8 is provided with a mobile base 10 (e.g., locking wheels) so that the system 2 is easily moveable and steerable. However, those of skill in the art will understand that the base 10 may be static or that electronic control and movement of the system 2 may also be implemented.

Figure 2:
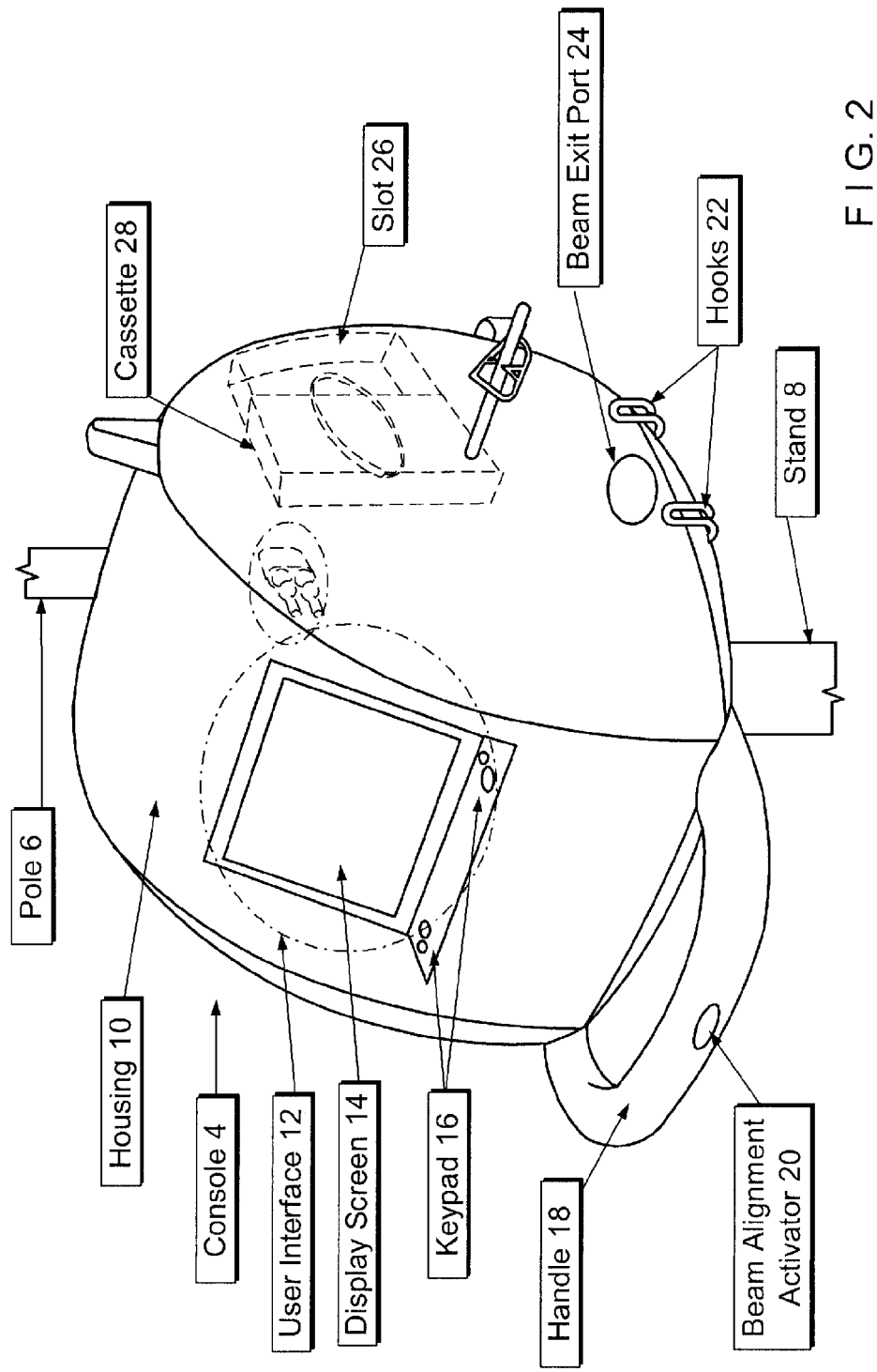
FIG. 2 shows a frontal view of an exemplary embodiment of a console of a thermal ablation system according to the present invention.

As shown in FIG. 2, the console 4 according to the present invention comprises a housing 10 encasing electronic circuitry and providing a user interface 12 for displaying content (e.g., instructions, procedural data, warnings, etc.) and receiving user input. The user interface 12 may comprise a display screen 14 (e.g., LCD) and a keypad 16 for submitting input to the console 4. Those of skill in the art will understand that the keypad 16 may be replaced or augmented by dials, switches, a touch screen (or the screen 14 may be made responsive to tactile input) or any other controls operable by the operator of the system 2. In one exemplary embodiment, a disposable overlay (not shown) may be applied over the user interface 12. For example, if the display screen 14 is a touch screen and the operator intermittently provides input to the user interface 12 by touching the display screen 14, an overlay may be used to prevent the display screen 14 from becoming damaged or obscured by fluid.

The housing 10 may further include a handle 18 for steering the system 5 and a slot 26 receiving a cassette 28, which is described below. In the exemplary embodiment, the handle 18 includes an alignment beam activator 20 which, when pressed, causes a light beam (e.g., laser light) to be emitted from a beam exit port 24 on the console 4. As would be understood by those skilled in the art, the light beam may preferably be oriented horizontally so that, as the height of the console 4 is adjusted using the height adjusting mechanism on the stand 8 until the beam is positioned on a desired portion of the patient's anatomy, the operator will know that the console 4 is in a desired position relative to the uterus (e.g., level with the uterus). Making the console 4 a desired height off the floor relative to the uterus (e.g., the same height) ensures that a pressure at which the fluid is circulated in the uterus does not exceed a predetermined value. Those of skill in the art will understand that the activator 20 may be disposed adjacent to the user interface 12 and/or the keypad 16 or may be positioned on the handle 18. The housing 10 preferably also includes a hook 22 for hanging a drainage bag (not shown) from the console 4. After ablating the endometrial lining, the fluid is discharged into the drainage bag.

Figure 3:
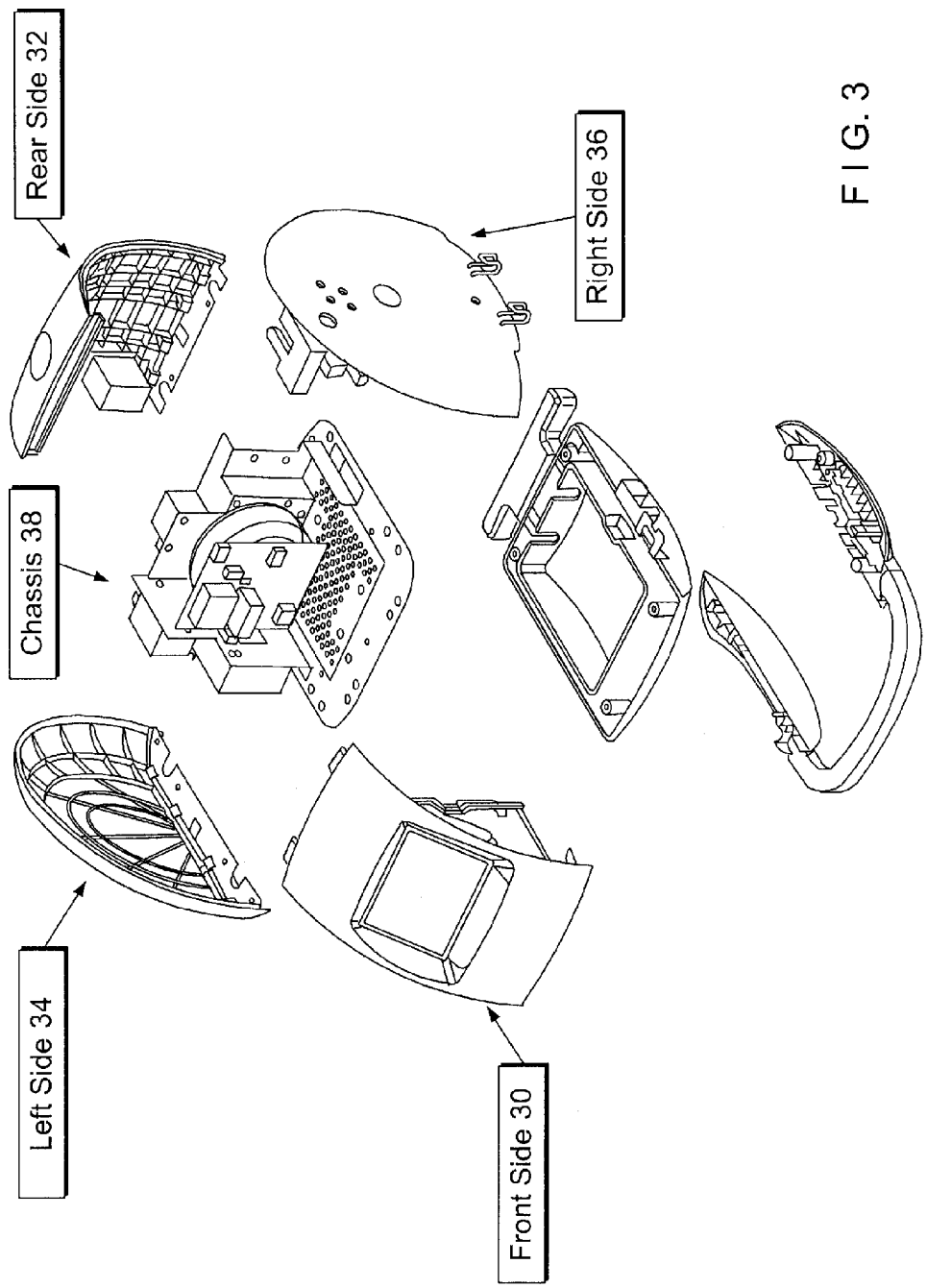
FIG. 3 shows an exploded view of an exemplary embodiment of a console of a thermal ablation system according to the present invention.

FIG. 3 shows internal components of an exemplary console 4 according to the present invention. The housing 10 of the console 4 includes a front side 30, a rear side 32, a left side 34 and a right side 36. Those of skill in the art will understand that the housing 10 may be comprised of any number of components in any number of geometrical relationships to one another and that the terms front, rear, left and right are relational terms used only to describe the exemplary embodiment of the console 4. A chassis 38 inside the housing 10 acts as an attachment point for the sides 30, 32, 34, 36 and supports various electrical components of the console 4. In this embodiment, the front side 30 includes circuitry powering the user interface 12 and the beam activator 20, while the rear side 32 provides an input for a power source (e.g., line voltage). However, in other exemplary embodiments, the system 2 may be powered by an on-board battery. The left side 34 generally comprises a vented wall which allows air heated during operation of the electric components of the console 4 to be expelled therefrom, while the right side 36 includes components that interface with the cassette 28.

Figure 4:
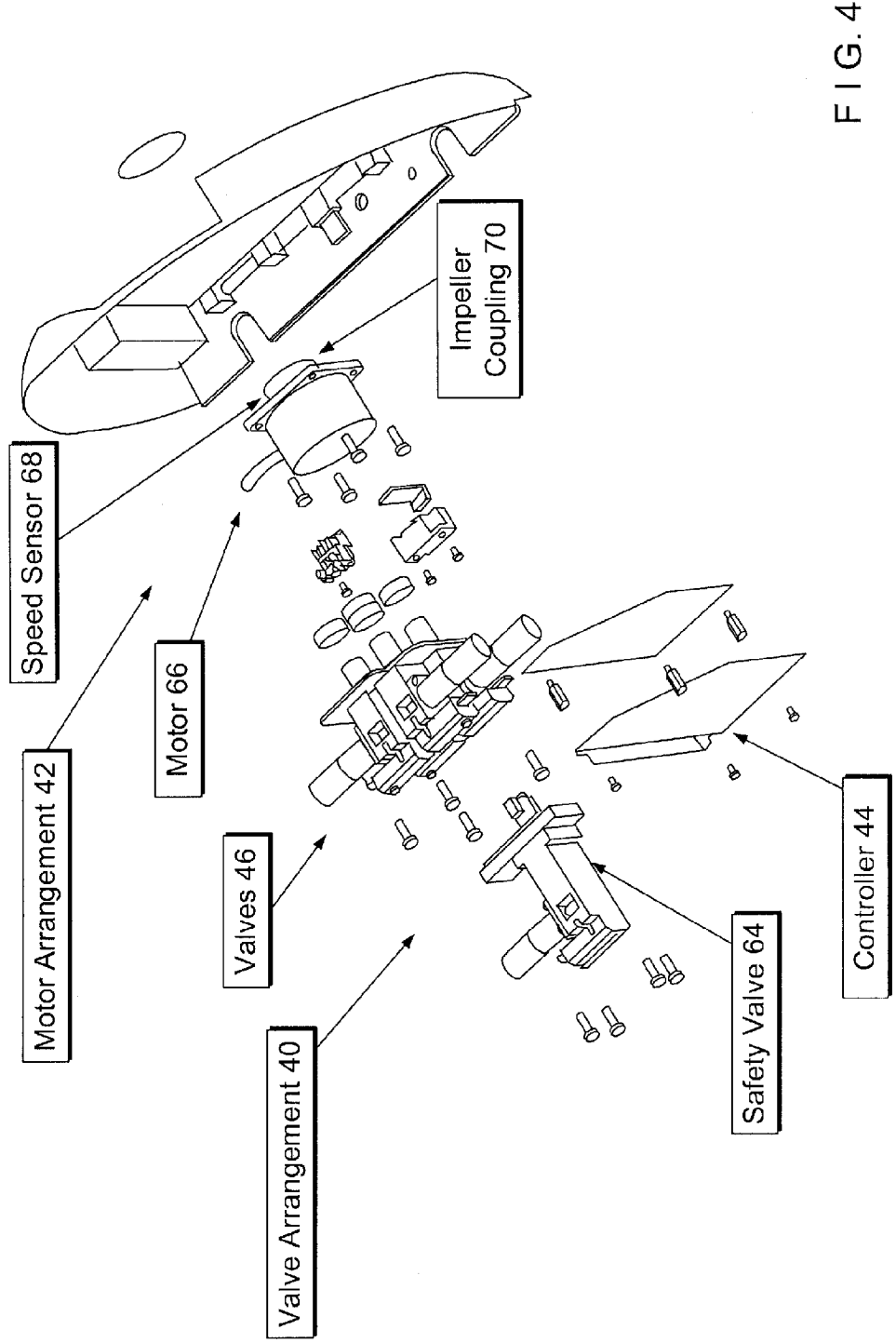
FIG. 4 shows an exploded view of an exemplary embodiment of a right side component of a console of a thermal ablation system according to the present invention.
Figure 5:
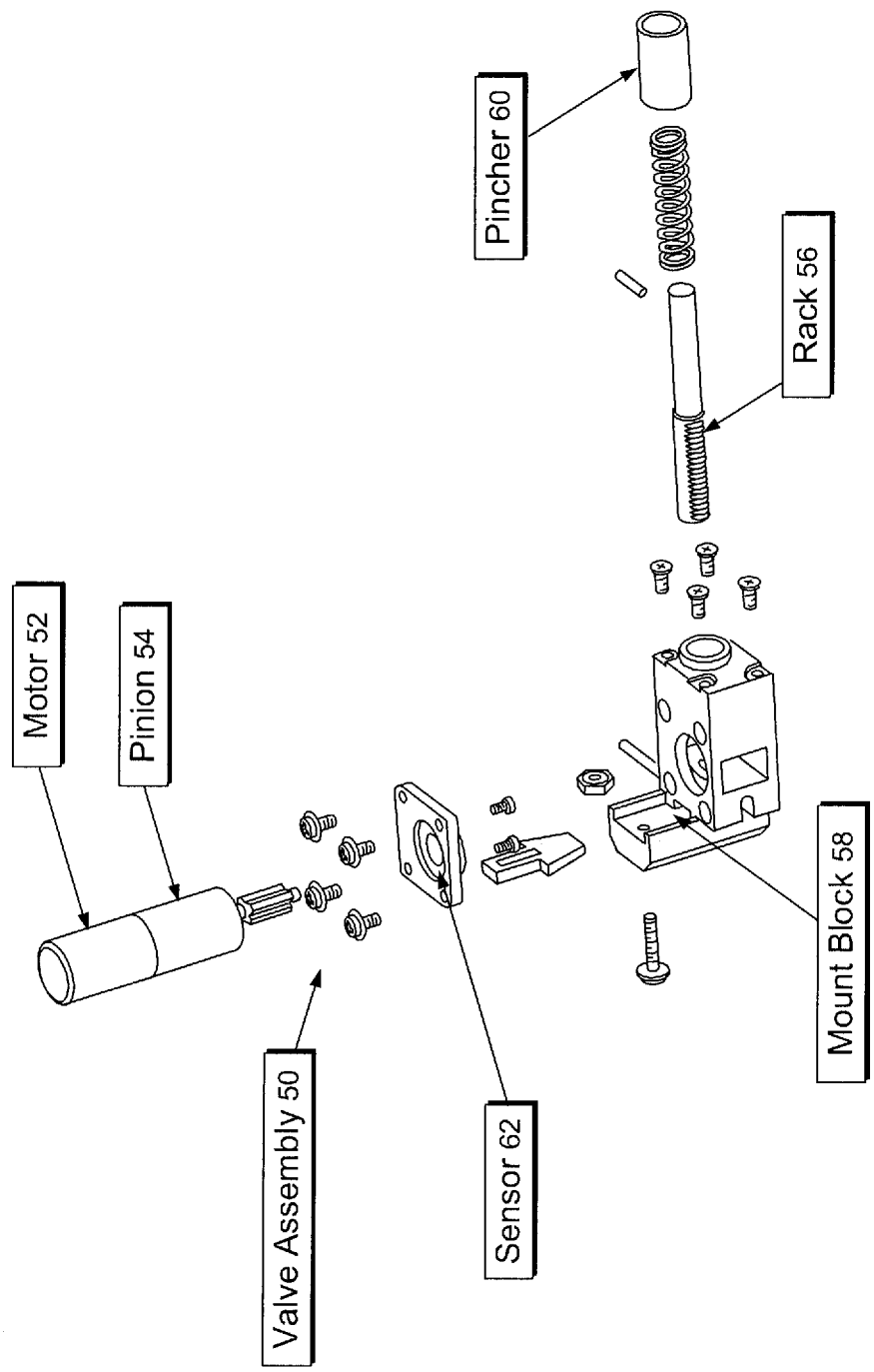
FIG. 5 shows an exploded view of an exemplary embodiment of a valve assembly for a console of a thermal ablation system according to the present invention.

FIG. 4 shows an exemplary embodiment of the right side 36 of the console 4 which includes components for interfacing with the cassette 28. The cassette interface generally includes a valve arrangement 40 and a motor arrangement 42. The valve arrangement 40 includes one or more valves 46 (e.g., pinch valves) which engage outer surfaces of flexible tubes within the cassette 28 via openings in a rigid housing thereof to selectively open and close the tubes without contacting fluids flowing therethrough. As shown in FIG. 5, an exemplary valve assembly 50 is a pinch valve. However, those of skill in the art will understand that the functions of the valves 46 may be performed by any device(s) configured to selectively open and close the tubes in the cassette 28 without contacting fluids within the tubes.

As shown in FIG. 5, the valve assembly 50 includes a motor 52 which drives rotation of a pinion 54 that mates with a rack 56. Rotation of the pinion 54 is translated into axial movement of the rack 56 in distal (lumen-closing) and proximal (lumen-opening) directions relative to a mount block 58 with a pincher 60 coupled to a distal end of the rack 56. As the rack 56 is driven distally by the rotation of the pinion 54, the pincher 60 compresses a respective lumen in the cassette 28 against a wall of the cassette 28. A position sensor 62 (e.g., an optical sensor, Hall effect sensor, etc.) may be included in the valve assembly 50 to determine a position of the pincher 60 relative to the respective lumen. In this manner, an amount of closure of the respective lumen and/or an amount of fluid flow permitted through the respective lumen at the amount of closure may be determined. As will be described further below, the system 2 may utilize the closure information to adjust a volume and/or pressure of fluid circulated through the uterus.

Referring back to FIG. 4, the valves 46 may include a number of valve assemblies 50 including similar rack and pinion assemblies and pincer combinations or other mechanisms corresponding to a number of lumens in the cassette 28 to be selectively opened and closed. The valve arrangement 40 may further include a safety valve 64 which opens whenever a pressure within the lumen exceeds a predetermined maximum pressure or whenever an unsafe condition is detected.

The motor arrangement 42 includes a motor 66 (e.g., a DC brushless motor), a speed sensor 68 and an impeller coupling 70. Current supplied to the motor 66 rotates an armature thereof which, in turn, rotates the impeller coupling 70. In one exemplary embodiment, the impeller coupling 70 includes one or more magnets which, when the cassette 28 is inserted into the console 4, are magnetically coupled to one or more magnets on an impeller in the cassette 28 so that rotation of the impeller coupling 70 rotates the impeller to drive fluid through the cassette 28 and into the patient with no contact between fluid in the cassette 28 and components of the console 4 outside the cassette 28. Those of skill in the art will understand that the impeller coupling 70 and the impeller are an exemplary embodiment of any pump arrangement which may be used to output fluid from the cassette 28. The speed sensor 68 may be coupled to the motor 66 to detect a rotational speed of the armature thereof to determine, for example, a speed (and/or pressure) at which fluid is being circulated through the cassette 28 and/or the uterus.

Figure 6:
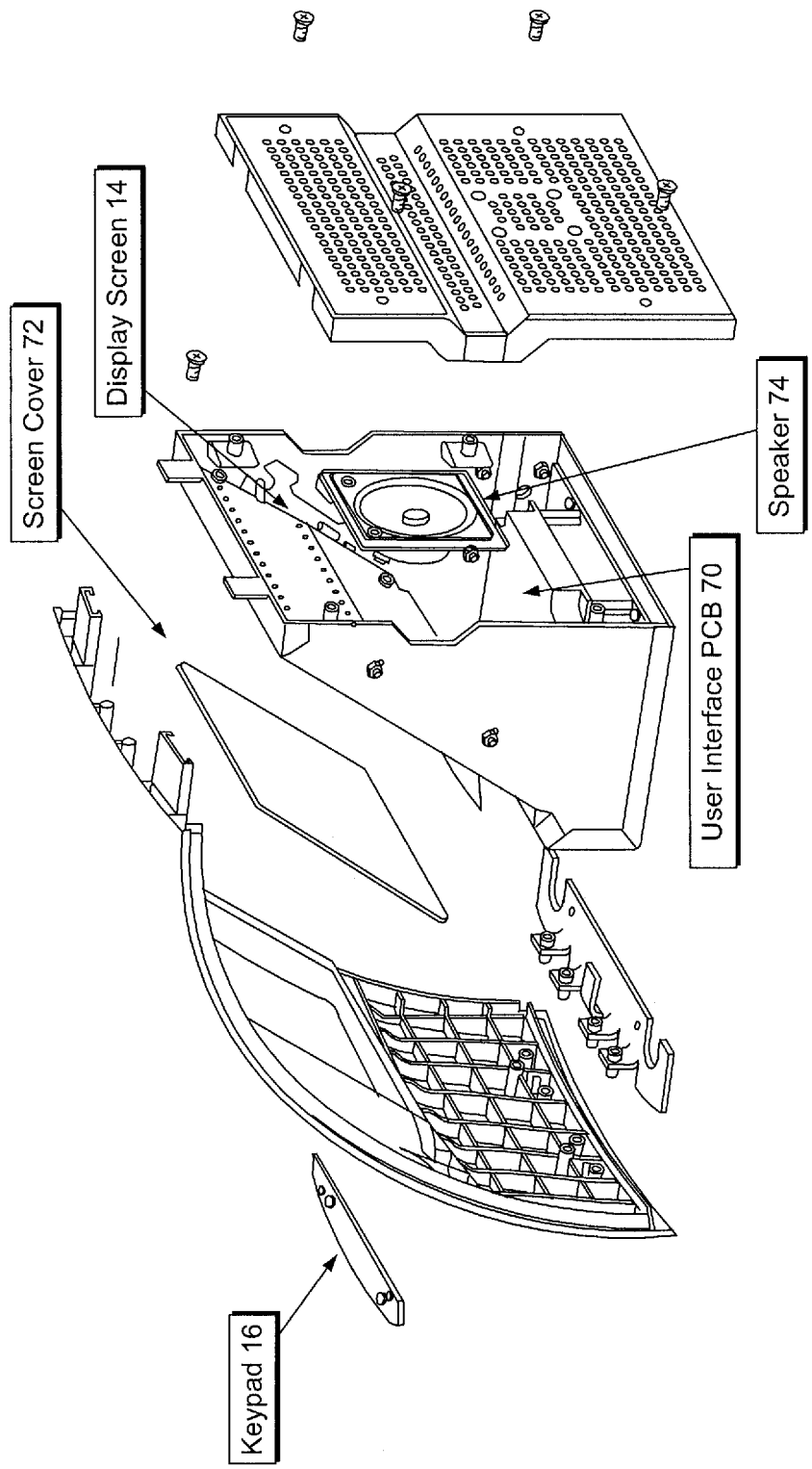
FIG. 6 shows an exploded view of an exemplary embodiment of a front side component of a console of a thermal ablation system according to the present invention.

As shown in FIG. 6, an exemplary embodiment of the front side 30 of the console 4 includes the user interface 12, the display screen 14 and the keypad 16 which may be controlled by a user interface printed circuit board (PCB) 70 which interprets user input entered via the keypad 16 and displays the content on the display screen 14. A screen cover 72 may be overlaid on the display screen 14 to protect and allow cleansing thereof. The disposable overlay described above is preferably overlaid on the screen cover 72. A speaker 74 disposed within the console 4 may be utilized to provide to the operator audible signals such as, for example, voice instructions, warning signals, etc. which, when used in conjunction with the visual content presented on the display screen 14 facilitate operation of the system 2. Additionally, the audible output may be useful when, for example, two persons are working in conjunction to perform the ablation procedure. That is, the operator may be monitoring operation of the system 2, while a physician and/or nurse may be monitoring the fluid circulation through the uterus. The audible output makes both persons aware of the progress of the ablation procedure regardless their fields of view.

Figure 7:
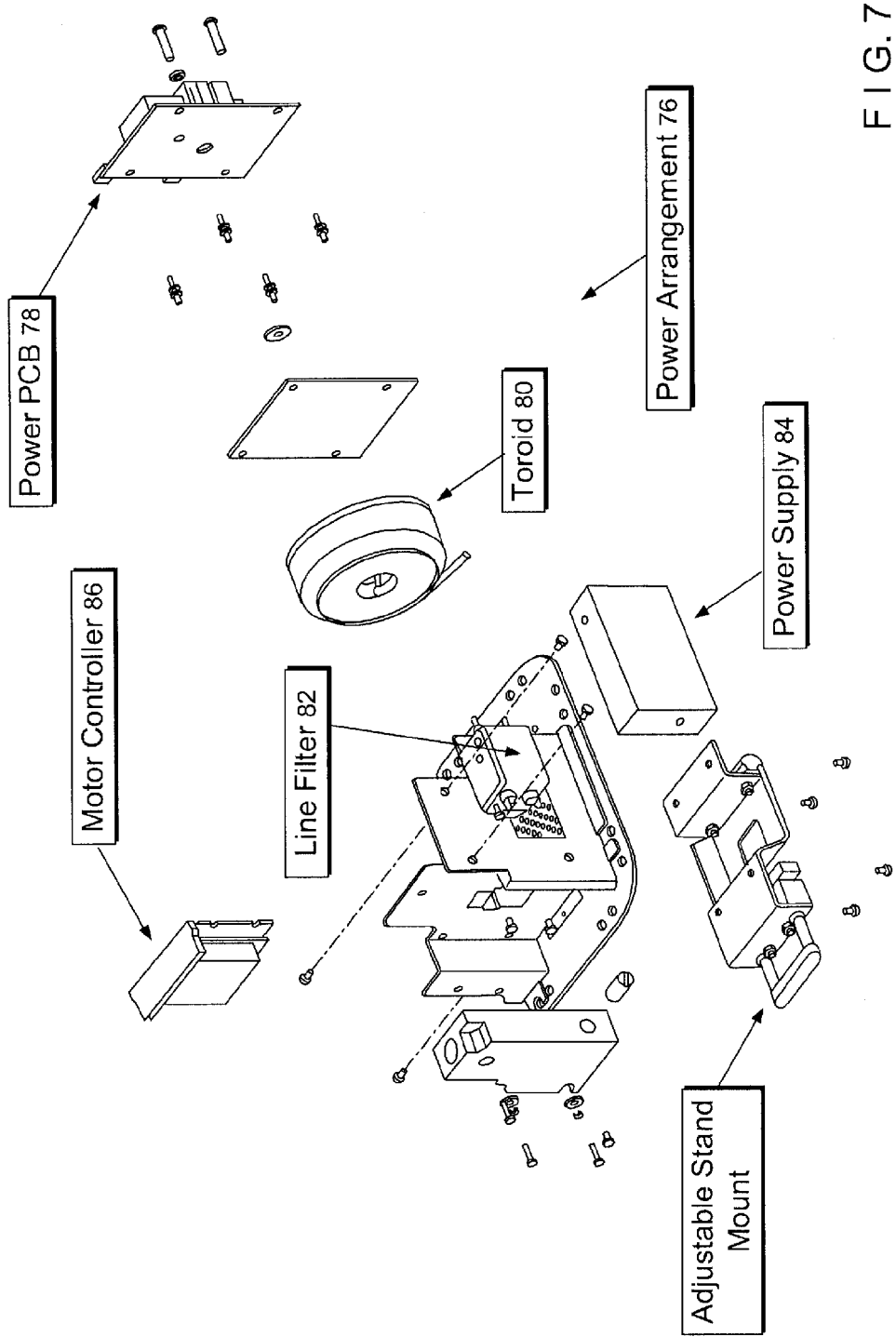
FIG. 7 shows an exploded view of an exemplary embodiment of a chassis of a console of a thermal ablation system according to the present invention.

As shown in FIG. 7, the chassis 38 in the console 4 according to the exemplary embodiment is encased by the right, left, front and rear sides 30, 32, 34, 36 of the housing 10. A power arrangement 76 mounted on the chassis 38 includes a power PCB 78, a toroid 80, a line filter 82 and a power supply 84 coupled to, for example, a port for receiving a line voltage. For example, the power supply 84 may have a power cord extending therefrom to be plugged into a wall outlet, or the port may receive a plug as part of an extension cord. The line filter 82 treats the power to, for example, eliminate surges, harmonic transient currents, spikes, etc. in the current being delivered to the console 4. The filtered current is then transmitted to the power PCB 78 which distributes power to operational components of the system 2. The toroid 80 operates as a transformer, providing electrical isolation between circuits in the console 4.

Also mounted on the chassis 38 is a motor controller 86 which receives instructions from a controller 44 to control operation of the motor 66. The controller 44, which is shown in FIG. 4, may be a central processing unit which coordinates operation of the system 2 during the ablation procedure. That is, the controller 44 may process an instruction set stored in a memory for controlling the user interface 12, the motor 66, the valves 46, the safety valve 64, etc. during the ablation procedure. An exemplary use of the system 2 for performing an ablation procedure will be explained in more detail below.

Figure 9:
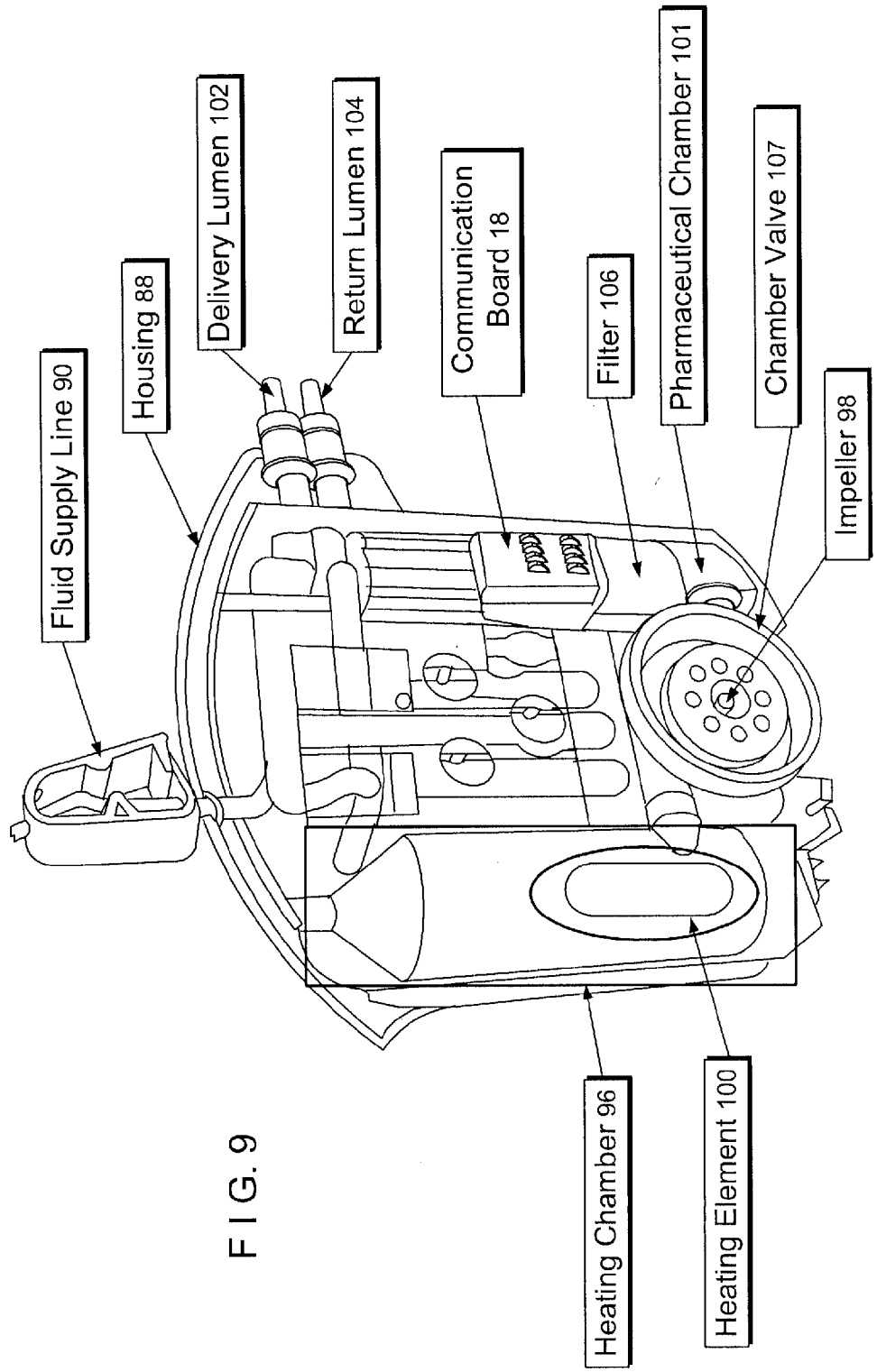
FIG. 9 shows an inner view of an exemplary embodiment of a cassette of a thermal ablation system according to the present invention.

FIGS. 8 and 9 show an exemplary embodiment of the cassette 28 according to the present invention. As noted above, the cassette 28 may be embodied in a housing 88 sized and shaped to fit within the slot 26 on the console 4. For example, the housing 88 may include rails along its sidewalls which are received by guides on the sidewalls of the slot 26, allowing the cassette 28 to slide thereinto. Once in the slot 26, the cassette 28 may be mechanically locked in place (e.g., latches, hooks, etc.), gravitationally held in the slot 26, magnetically coupled to the console 4, etc. In one exemplary embodiment, the instructions provided on the user interface 12 may instruct the operator on how and when to insert and remove the cassette 28. The console 4 may lock the cassette 28 in the slot 26 to prevent removal during an ablation procedure.

The fluid from the IV bag enters the cassette 28 via a fluid supply lumen 90 which terminates in a reservoir 92. In this embodiment, a level sensing board 94 is disposed within the reservoir 92 for monitoring a volume of fluid therein. During the ablation procedure, the controller 44 compares the volume to a predetermined volume (or range thereof) to determine whether fluid has been lost/leaked. Based on the results of the comparison, the system 2 may shut down or execute a predetermined safety procedure. In the exemplary embodiment, the level sensing board 94 comprises a plurality of level sensors (e.g., capacitors) arranged along a height of the board 94. By analyzing signals received from the level sensors, the controller 44 may determine the volume of the fluid within the reservoir 92.

The safety procedure may be a set of instructions stored in a non-volatile memory of a complex programmable logic device (CPLD) in the console 4. Based on the results of the comparison, the controller 44 may transmit a safety procedure initiation signal to the CPLD which then executes the safety procedure. The safety procedure may also be executed if, for example, the controller 44 indicates that a component of the system 2 is non-responsive or otherwise malfunctioning. The CPLD may also execute the safety procedure if the controller 44 malfunctions.

The fluid in the reservoir 92 is directed into a heating chamber 96 by an impeller 98 which, as described above, is rotated by the impeller coupling 70 in the console 4. As shown in FIGS. 14 and 15, an exemplary embodiment of the impeller 98 includes a plurality of veins 160 disposed on a first surface and a plurality of magnets 162 disposed on a second surface. Each of the veins 160 may be formed, for example, as a concave projection on the first surface and have a predefined spacing and angle relative to adjacent veins. In this configuration, the fluid interfacing with the impeller 98 is forced from a center of rotation thereof and into the heating chamber 96. The magnets 162 may be embedded in the impeller 98 having exposed surfaces flush with the second surface which magnetically couple to the magnets on the impeller coupling 70. An interface between the impeller 98 and the impeller coupling 70 may be configured so that only the first surface of the impeller 98 comes into contact with the fluid, while the second surface is exposed on (and/or forms a part of) an external surface of the cassette 28. Alternatively, the impeller 98 may be fully enclosed within the cassette 28.

The heating chamber 96 includes a heating element 100 which heats the fluid therein. Operation of the heating element 100 may be based on a temperature measurement of the fluid obtained by a temperature sensor (e.g., thermistor) in the heating chamber 96. By monitoring the temperature measurement, the controller 44 ensures that the fluid temperature is within a predetermined range (e.g., a temperature hot enough to ablate tissue). Those of skill in the art will understand that the heating element 100 may further include a cooling element or be deactivated when, for example, the ablation procedure has been completed and the remaining surface tissue in the uterus is to be allowed to cool or when a safety procedure is executed.

As shown in FIG. 13, the heating chamber 96, in this embodiment, is substantially cylindrical with a fluid inlet 150 at a lower end thereof. The inlet 150, which receives fluid pumped from the impeller 98, is directed substantially tangential to the cylinder so that the fluid swirls around the heating chamber 96 and is heated by the heating element 100 as it rises to an outlet at the top of the cylinder. The heating element 100 extends substantially along a longitudinal axis of the cylinder so that the fluid travels around the heating element 100 in a substantially helical path as it rises in the heating chamber 96, maximizing energy transfer to the fluid.

When the fluid exits the heating chamber 96 after having reached the desired temperature, it leaves the cassette 28 via a delivery lumen 102 and passes into an introducer which is inserted into the uterus via the cervix. The fluid is circulated through the uterus and returned to the cassette 28 via a return lumen 104. The returned fluid is then passed through a filter 106 to remove any tissue remnants, coagulated plasma, etc. and fed back through the impeller 98 into the heating chamber 96. By continuously circulating the returned fluid while monitoring any volumes of fluid added/removed from the system 2, the controller 44 detects any change from the initial fluid volume as described above to determine a volume of fluid absorbed into the body. When the ablation procedure has been completed, the fluid is drained into the drainage bag via a drainage lumen 110.

Electrical signals generated by the temperature sensors in the heating chamber 96 and the level sensors in the reservoir 12 are transferred to the controller 44 via a communications circuit board 108 and digitized. The digitized signals are then converted into procedural data (e.g., temperature data and volume data) which is analyzed by the controller 44 to monitor the progress of the ablation procedure.

Figure 11:
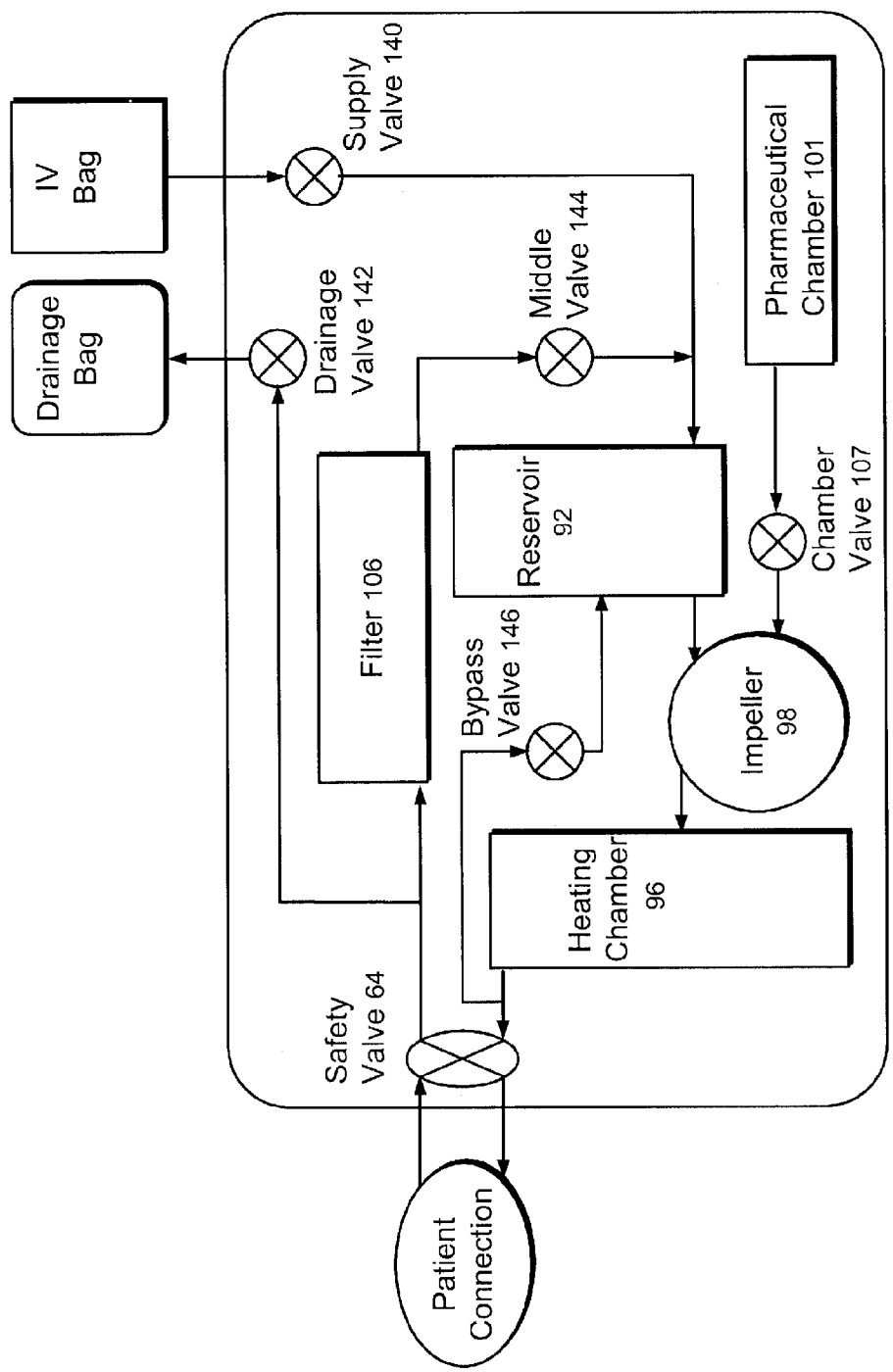
FIG. 11 shows an exemplary embodiment of an open loop fluid flow path of a thermal ablation system according to the present invention.
Figure 12:
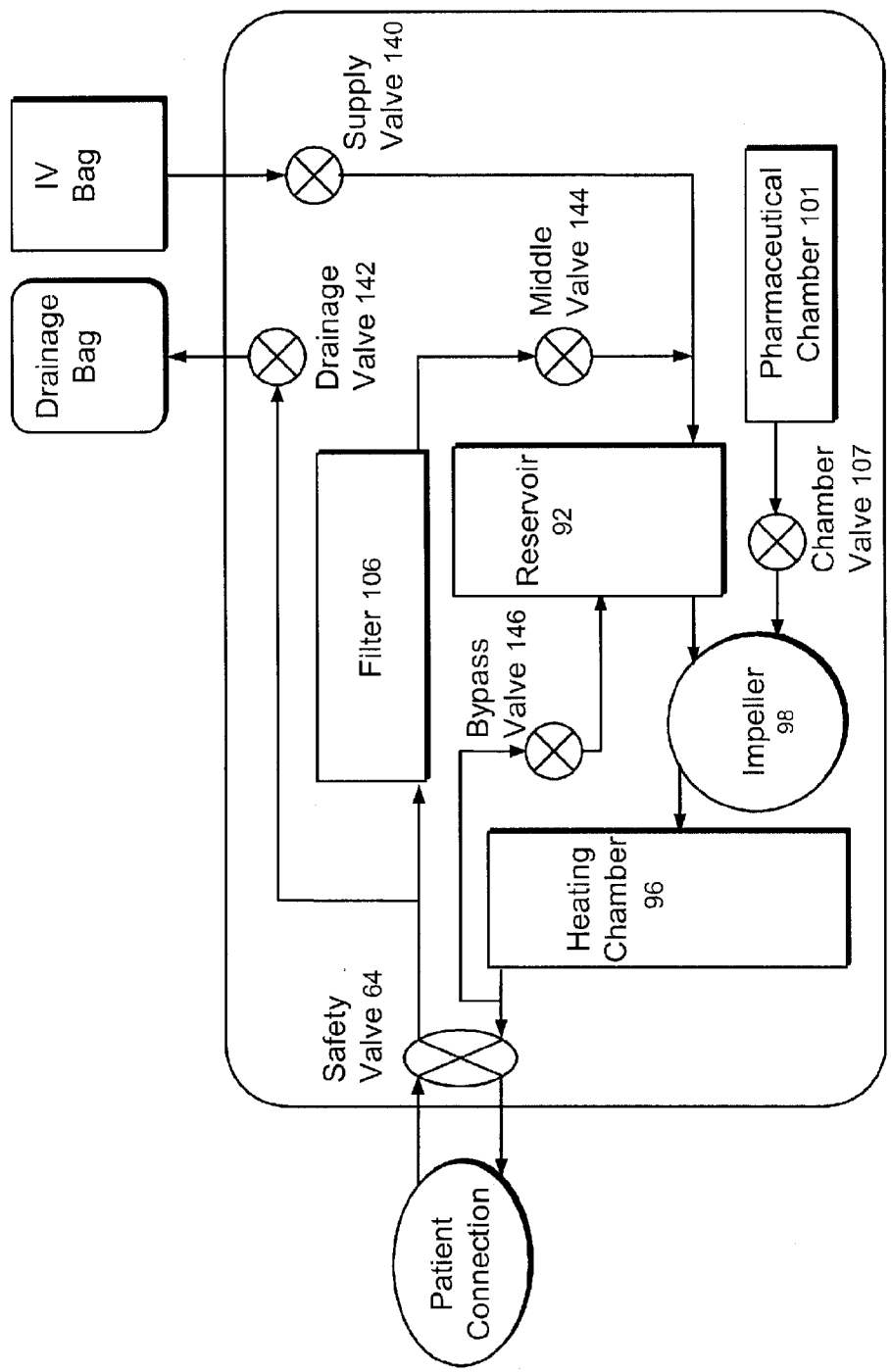
FIG. 12 shows an exemplary embodiment of a closed loop fluid flow path of a thermal ablation system according to the present invention.

During progression of the ablation procedure, the controller 44 configures alternative fluid flow paths through the cassette 28 by selectively controlling operation of the valves 46 to open and close the fluid flow lumens therein. FIG. 11 shows an open loop flow path used during priming and/or cooling stages of the ablation procedure. For example, the system primes by opening the supply valve 140 to permit fluid from the IV bag through the cassette 28 to the reservoir 92 and through the impeller 98 to the heating chamber 96 which is inactive at this point through the safety valve 64 into a delivery (not shown) of an introducer 112. The fluid exits the delivery lumen into the uterus and is drawn back from the uterus into a return lumen (not shown) of the introducer 112 which passes the fluid back through the safety valve 64 and out to a drainage bag via a drainage valve 142. When the system has been primed, the valves of the cassette 28 are reconfigured to the closed loop configuration of FIG. 12 for heating of the fluid and ablation. Specifically, the drainage valve 142 is closed so that fluid circulates from the reservoir 92, through the impeller 98 and the heating chamber 96 and into the uterus via the safety valve 64 and the introducer 112. The fluid returning from the uterus via the return lumen 104 of the introducer 112 passes through the safety valve 64 and the filter 106 to return to the reservoir 92 via the middle valve 144 and continues to circulate through this path during the ablation procedure. In this configuration, the heating chamber 96 is active to raise the temperature of the fluid to a desired level for ablation. In addition, in this configuration, the bypass valve 146 is opened when necessary to bleed off excess flow from the output from the heating chamber 96 returning this bled-off fluid to the reservoir 92 without passing through the uterus. When the procedure has been completed, the drainage valve 142 is opened and the bypass valve 146 and the middle valve 144 are closed to return the system 100 to the open-loop configuration of FIG. 11. The heating chamber 96 is deactivated at this point so that fluid currently circulating in the cassette 28 flows through the uterus and passes through the drainage valve 142 to the drainage bag without further heating. After this fluid has been drained, fresh fluid from the IV bag is passed through the cassette 28 into the uterus at substantially room temperature to flow out into the drainage bag until a desired amount of cooling has been achieved. As would be understood by those skilled in the art, cooling may also be performed by continuing to circulate the fluid through the closed loop while the heating element is powered off.

Referring back to the exemplary embodiment of the cassette 28 shown in FIG. 8, a therapeutic agent chamber 101 may be formed in the cassette 28 for storing a predetermined volume of a therapeutic agent. For example, up to 30 cc's of diluted or concentrated fluid may be stored in the therapeutic agent chamber. The therapeutic agent is retained in the chamber 101 by a chamber valve 107 which is selectively opened and closed by the controller 44 to open and close an output lumen of the chamber 101 in coordination with the ablation procedure. When the chamber valve 107 is open, the therapeutic agent is permitted to flow to the impeller 98 (e.g., by gravity, suction created by rotation of the impeller 98, etc.) via the output lumen and be pumped out of the cassette 28 into the uterus, as will be explained further below. In the exemplary embodiment, the therapeutic agent stored in the chamber 101 may be a non-steroidal anti-inflammatory agent, a steroid, an analgesic (e.g., Ketorolac Tromethamine), an antimicrobial agent, an anesthetic or any combination thereof which may be used to reduce inflammation, discomfort, possibility of infection or any other deleterious effect associated with ablating tissue or any other therapeutic agent. Preferably, the chamber 101 is thermally isolated within the cassette 28, preventing adverse thermal effects to the therapeutic agent during operation of the heating element 100. In another exemplary embodiment, an external therapeutic agent source is coupled to the cassette 28 via the fluid supply line 90 instead of or in addition to using the chamber 101.

After being circulated through the uterus and ablating the endometrial lining, the heated fluid is cooled and recirculated through the uterus to cool the uterine tissue. The controller 44 may then configure the valves 46 to the open loop configuration to purge the cassette 28 of the fluid and subsequently reconfigure the valves 46 for the closed loop configuration to circulate the therapeutic agent through the uterus. To release the therapeutic agent into the fluid flow path in the cassette 28, the controller 44 closes the supply, drainage and bypass valves 140, 142, 146 and opens the chamber and middle valves 107, 144. The therapeutic agent is released from the chamber 101 into the impeller 98 and is pumped through the heating chamber 96 (with the heating element 100 deactivated), out of the cassette 28 and into the uterus. Upon return from the uterus, the therapeutic agent is passed through the filter 106, into the reservoir 92 and back into the impeller 98 for recirculation out of the cassette 28 and into the uterus. Circulation of the therapeutic agent may occur for a predetermined time selected so that the therapeutic agent has the intended therapeutic effect (e.g., is absorbed by and/or coats the uterine tissue).

Those of skill in the art will understand that the cassette 28 may include any number of therapeutic agent chambers with each holding any type of therapeutic agent. In an exemplary embodiment with multiple therapeutic agent chambers, the controller 44 may manipulate chamber valves corresponding to each of the chambers in conjunction with the ablation procedure. For example, a first chamber may include a steroid, while a second chamber may include an antimicrobial agent. The controller 44 may selectively open and close the corresponding chamber valves to circulate the steroid and the antimicrobial agent through the uterus successively or concurrently at desired times before, during and/or after the procedure.

In one exemplary embodiment, a resealable port (not shown) may be disposed on the cassette 28 allowing a therapeutic agent to be injected to and/or removed from the chamber 101. In this embodiment, the cassette 28 may be reusable between patients or for a single patient. For example, if additional volume of the therapeutic agent is required (e.g., based on the surgical procedure), the physician may re-fill the chamber 101 with the therapeutic agent via the resealable port.

Figure 10:
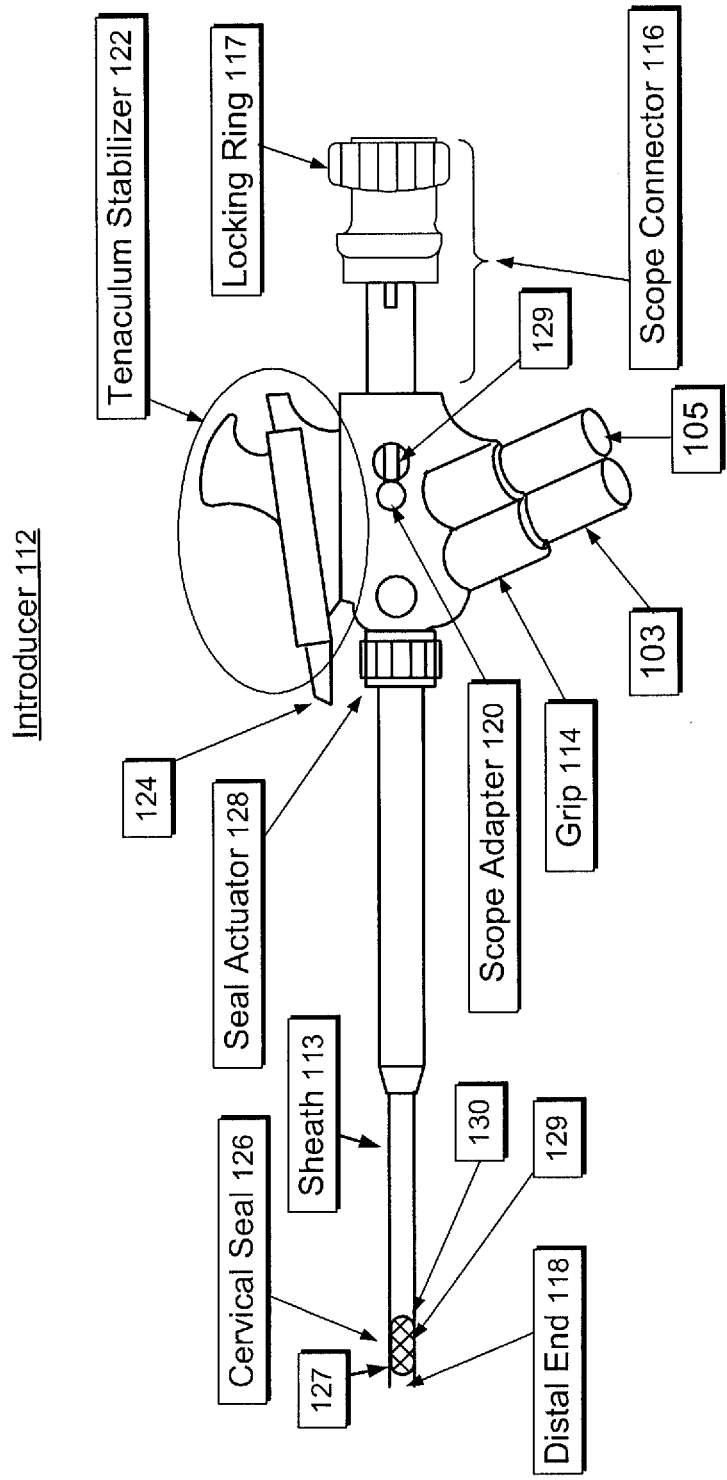
FIG. 10 shows an exemplary embodiment of an introducer of a thermal ablation system according to the present invention.

As shown in FIG. 10, an introducer 112 according to an exemplary embodiment of the present invention is coupled to the cassette 28 via tubes 103 and 105 to deliver fluid to the uterus and to return the fluid from the uterus to the cassette 28. The tubes 103, 105 are coupled to the delivery and return lumens 102, 104, respectively, of the cassette 28 and to fluid delivery and return lumens (not shown) within a sheath 113 of the introducer 112. The fluid delivery and return lumens terminate at respective openings at a distal end 118 of the sheath 113 which, when the introducer 112 is in an operative positions, is located within the uterus. The introducer 112 may optionally include a vision system to allow visualization of the operative area. Those of skill in the art will understand that the vision system may be substantially similar to the systems in conventional endoscopes (e.g., fiber optic or CCD-based systems). Alternatively, users may rely on the vision system of an endoscope or other instrument inserted through the introducer 112, as described below.

The introducer 112 includes a grip 114 (e.g., an ergonomic handle) coupled to the sheath 113 and a scope connector 116 for receiving a visualization device, such as an endoscope. The grip 114 facilitates holding and manipulation of the introducer 112 with a single hand while the operator uses his free hand to interface with the console 4, adjust the visualization device, manipulate the patient's anatomy, etc. The scope connector 116 according to this embodiment is disposed on a proximal end of the introducer 112 and provides an attachment point for the visualization device (e.g., a hysteroscope, an endoscope) so that the visualization device may be passed distally through a visualization lumen in the introducer 112 and extended out of the distal end 118. Thus, the operator may visually monitor insertion of the introducer 112 into the uterus.

The scope connector 116 may comprise an optional locking ring 117 and a scope adapter 120 which allow the introducer 112 to be adjusted to accommodate visualization devices of varying lengths. The visualization device is inserted into the proximal end of the introducer 112 through the scope connector 116 and locked thereto using the locking ring 117. The user then depresses the scope adapter 120 releasing the scope adapter 120 from a current locking aperture 121. This allows the scope connector 116 to slide proximally out of or distally into the introducer 112 so that, when the visualization device has been inserted through the sheath 113 to a desired position in the uterus, the scope connector 116 supports the portion of the visualization device extending out of the introducer (e.g., a proximal end of an endoscope immediately distal of the control handle). Those of skill in the art will understand that the scope connector 116 may be implemented as any mechanism which allows the length of the introducer 112 to be adjusted to and maintained at a new length. For example, as shown in FIG. 10, the scope adapter 120 is formed as a projection on an outer surface of a distal portion of the scope connector 116 received in and movable between one of a number of locking apertures 121 formed on the grip 114. Partial barriers may be formed between each of the locking apertures 121 to retain the scope adapter 120 in a selected one of the locking apertures 121 maintaining a selected length of a portion of the scope connector 116 projecting from the proximal end of the introducer 112. In another embodiment, a rack may be formed on the distal portion of the scope connector 116 mating with a gear in the grip 114 so that rotation of the gear extends and withdraws the scope connector 116 relative to the grip 114. A ratchet may be provided to maintain the gear in a fixed position relative to the rack, thereby maintaining the desired position of the scope connector 116 relative to the grip 114.

The grip 114 may further include an optional tenaculum stabilizer 122. For example, during the ablation procedure, a tenaculum may be employed around the cervix to enhance the seal of the cervix around the sheath 113 of the introducer 112. A tenaculum that has been clamped around the cervix may then be coupled to the introducer 112 to ensure that the introducer 112 remains at a desired position within the uterus and is not inadvertently withdrawn therefrom. That is, it is important to make sure that the distal end of the sheath 113 is not withdrawn proximally from the uterus during the procedure or non-targeted tissue will be exposed to the ablation fluid. Thus, a portion of the tenaculum is passed over the tenaculum stabilizer 122 preventing movement of the sheath 113 proximally relative to the tenaculum. That is, once a tenaculum has been locked in position on tissue, the tenaculum can be slipped over the tenaculum stabilizer 122. The tenaculum stabilizer 122 is moved to a proximal-most position permitted by the tenaculum. Specifically, in the exemplary embodiment, the tenaculum stabilizer 122 includes a fin slidably mounted on a rail 124 formed on the grip 114. The fin includes a hook which may receive finger grips or a crossbar of a tenaculum as would be understood by those skilled in the art. When the tenaculum is coupled to the tenaculum stabilizer 122, the operator selects a tension to be applied between the tenaculum and the introducer 112 by moving the fin along the rail 124. A positioning mechanism (e.g., ratchet, latch, clip, etc.) may be used to maintain a position of the fin relative to the rail 124, as would be understood by those skilled in the art. Such a tenaculum stabilizer device is described in a U.S. Provisional Patent Application Ser. No. 60/971,409 filed on Sep. 11, 2007 and entitled "TENACULUM STABILIZER DEVICE," naming as inventors Christopher Oskin, Brian MacLean, Stephen Keaney, Jozef Slanda and Jeffrey Zerfas. The entire disclosure of this application is hereby incorporated by reference herein.

The introducer 112 may further include an optional cervical seal 126 separated from a distal end of the sheath 113 by a distance selected to ensure that, when the distal end of the sheath 113 is in a desired position within the uterus, the seal 126 is located within the cervix proximal to the cervical os C. When the distal end 118 of the introducer 112 is introduced into the uterus, the elasticity of the cervix provides a substantially fluid-tight seal around the sheath 113. However, to minimize the risk of ablation fluid escaping through the cervix to damage non-targeted tissue, the fluid-tight seal may be enhanced/maintained using the cervical seal 126. In the exemplary embodiment, the cervical seal 126 is formed as a flexible membrane 127 which overlies a wire mesh 129, a proximal end of which abuts a distal end of an expander member 130. The wire mesh 129 may, for example, be formed as a PEEK braid or an SS braid while the membrane 127 may, for example, be formed of silicone, a rubber material, or C-Flex. A distal end of the cervical seal 126 is fixed to the sheath 113 while a proximal end is slidable along the sheath 113.

A seal actuator 128 comprises a ring rotatably mounted on the sheath 113 and coupled to the expander member 130 which, in this embodiment, is formed as an oversheath telescopically mounted over the sheath 113. The ring may be coupled to the oversheath in such a manner that rotation of the ring moves the oversheath proximally and distally over the sheath 113. For example, an outer portion of the proximal end of the oversheath may be threaded to mate with threads on an inner portion of the ring of the seal actuator 128 so that, when the ring is rotated in a first direction, the expander member 130 slides distally along the sheath 113 pushing the proximal end of the mesh 129 distally causing the cervical seal 126 to expand radially away from the sheath 113.

As shown in FIG. 16, it is preferable that expansion of the cervical seal 126 is executed when it is within the cervix proximal of the cervical os C so that none of the targeted tissue is covered by the seal 126. In the exemplary embodiment, the sheath 113 is moved distally until the distal end 118 thereof is within the uterus. The sheath 113 is then withdrawn proximally to minimize a projection of the sheath 113 into the uterus maximizing a field of view of the vision system. While in this position, the cervical seal 126 is positioned entirely within the cervix with a distal end of the seal 126 proximal of the cervical os C. The expander member 130 engages the proximal end of the cervical seal 126 and pushes the proximal end distally along the sheath 113 into the expanded position shown in FIG. 16. In the expanded position, the membrane 127 substantially engages an inner wall of the cervix enhancing the seal provided by the natural resilience of the wall of the cervix. The distal end of the seal 126 is preferably located approximately between 1 and 4 mm proximal of the distal end 118 of the sheath 113 and is more preferably approximately 2 mm proximal of the distal end 118. In addition, the seal 126 preferably expands to an OD of between 8 and 14 mm and more preferably expands to an OD of approximately 11 mm.

Rotation of the ring in a second direction withdraws the expander member 130, allowing the cervical seal 126 to return to its unexpanded state through the bias of the mesh 128 which tends toward the unexpanded state. Alternatively, the proximal end of the mesh 129 may be coupled to the distal end of the expander member 130 so that, as the expander member 130 is moved proximally, the mesh 129 is drawn back into the unexpanded state against a bias of the mesh 128 which tends to expand the seal 126.

In an exemplary use, the system 2 according to the present invention may be used to ablate the endometrial lining of the uterus. When the console 4 is activated, the display screen 14 may show (and the speaker 74 may provide) a pre-operative instruction set. For example, the instruction set may prompt the operator to hang the IV bag and the drainage bag. The controller 44 may then detect whether the cassette 28 has been inserted into the slot 26 and provide instructions regarding a procedure for connecting the cassette 28 to the IV bag, the drainage bag and the introducer 112. In addition, the controller 44 may determine, upon detecting the presence of the cassette 28, whether the cassette 28 has been previously used and prevent operation or take other pre-ordained steps if prior use is detected.

The pre-operative instruction set may also instruct the operator to adjust a height of the console 4 to be substantially equal with a height of the uterus or to achieve some other desired relationship between the height of the console 4 and that of the uterus. In the exemplary embodiment, the height of the console 4 is varied by adjusting the stand 8 using a light beam (e.g., laser) emitted from the beam exit port 24 to ensure that the console 4 is level with the uterus. When the console 4 is level with the uterus, the operator may initiate the ablation procedure by inserting the introducer 112 into the uterus via the cervix and expanding the cervical seal 126 within the cervix. The controller 44 may then configure the cassette 28 for the open loop flow path by opening the fluid supply and drainage valves 140, 142 and circulate a pre-operative fluid through the uterus, priming the endometrial lining for ablation.

During a heating stage of the ablation procedure, the fluid from the IV bag enters the cassette 28 and is heated to a predetermined temperature (e.g., approximately 85-90° C.) as indicated by signals generated by the temperature sensors in the heating chamber 96 and transferred to the controller 44 in the console 4 via the communications board 108. The signals may be digitized and analyzed to determine when the fluid has reached the predetermined temperature. Prior to the fluid being heated, the controller 44 configures the cassette 28 for the closed loop flow path by closing the fluid supply and drainage valves 140, 142 and opening the middle valve 144 so that fluid returning from the uterus is fed back into the reservoir 92, as described above.

When the fluid has reached the predetermined temperature, the console 4 initiates a treatment stage circulating the heated fluid through the introducer 112 into the uterus to ablate the endometrial lining as described above in regard to FIG. 12. The heated fluid is delivered to the uterus via the delivery lumen in the sheath 113, removed from the uterus via the removal lumen in the sheath 113 and returned to the console 4 where it is filtered by the filter 106 and returned to be circulated through the uterus for a predetermined duration (e.g., approximately 10 minutes) to ablate the endometrial lining. The treatment stage may further include a cooling cycle in which the heated fluid is allowed to cool and then circulated through the uterus to absorb heat from the exposed tissue aiding in the healing process. When the treatment stage has been completed, the console 4 employs a drain cycle, emptying the fluid in the system into the drainage bag.

In a post-treatment cycle, the controller 44 may configure the cassette 28 in the closed loop configuration and open the chamber valve 107, allowing the therapeutic agent in the chamber 101 to flow into the impeller 98. The therapeutic agent is then pumped out of the cassette 28 and into the uterus for circulation therethrough. When the therapeutic agent is removed from the uterus, it is passed through the filter 106 and into the reservoir 92. The level sensing board 94 may monitor a level of the therapeutic agent to ensure that a volume of the therapeutic agent being circulated through the uterus is substantially constant. However, those of skill in the art will understand that the volume may change, because a portion of the therapeutic agent may be absorbed by the uterine tissue, as medically intended.

Those of skill in the art will understand that various hardware and software-based variations may be implemented in the system 5 according to the present invention. For example, the height-adjusting mechanism on the stand 8 may be controlled by position data generated by a position sensor on the introducer 112. After the introducer 112 has been inserted into the uterus, the position data may be analyzed to determined a height of the introducer above the floor. If the height of the console 4 is not properly aligned with the height of the introducer 112, an alarm may be activated or an automatic height adjusting mechanism may adjust the height of the console 4 to the desired level. In addition, a pressure transducer may be coupled to the distal end 118 of the introducer 112 to sense the fluid pressure within the uterus. The pressure transducer may provide pressure data to the controller 44 which determines whether the pressure is within a predefined operable range, and if the pressure is outside of the range, the controller 44 may execute a safety procedure.

The present invention was described with reference to specific exemplary embodiments. Those skilled in the art will understand that changes may be made in details, particularly in matters of shape, size, material and arrangement of parts. For example, the invention is not limited to methods and devices for the thermal ablation of the uterine lining. Accordingly, various modifications and changes may be made to the embodiments. The specifications and drawings are, therefore, to be regarded in an illustrative rather than a restrictive sense.

What is claimed is:

1. A cassette for a heated fluid ablation system, comprising:
a fluid supply lumen receiving a fluid from an external fluid source;
a heating element heating the fluid to a desired temperature;
a fluid chamber containing a therapeutic agent;
an impeller pumping the fluid out of the cassette via a fluid delivery lumen; and
a valve arrangement altering a supply of fluid to the impeller so that, when the valve arrangement is in a first configuration, a first fluid flow path of the cassette in communication with the fluid supply lumen is open and a second fluid flow path of the cassette in communication with the fluid chamber is closed, and when the valve arrangement is in the second configuration, the first fluid flow path is closed and the second fluid flow path is open.

2. The cassette according to claim 1, wherein the fluid is saline.

3. The cassette according to claim 2, wherein the therapeutic agent is one of a non-steroidal anti-inflammatory agent, a steroid, an analgesic and an antimicrobial agent.

4. The cassette according to claim 1, wherein, when the valve arrangement is in the second configuration, receipt of the fluid is suspended.

5. The cassette according to claim 1, wherein, when the valve arrangement is in the first configuration, the therapeutic agent is stored in the fluid chamber.

6. The cassette according to claim 1, wherein the fluid chamber is thermally isolated within the cassette.

7. The cassette according to claim 1, further comprising a filter filtering the fluid and the therapeutic agent when returned to the cassette via a fluid return lumen coupled thereto.

8. An ablation system, comprising:
a console including a pump motor; and
a cassette detachably coupled to the console, the cassette receiving a fluid from an external fluid source and including an internal fluid chamber containing a therapeutic agent, the cassette including an impeller driven by the pump motor to output the fluid from the cassette via a fluid delivery lumen when the cassette is in a first configuration and output the therapeutic agent from the cassette via the fluid delivery lumen when the cassette is in a second configuration;
a heating element heating the fluid received by the cassette such that the fluid is at a desired temperature when outputted from the cassette; and
a valve arrangement altering a supply of fluid to the impeller so that, when the valve arrangement is in a first configuration, a first fluid flow path of the cassette in communication with the fluid supply lumen is open and a second fluid flow path of the cassette in communication with the fluid chamber is closed, and when the valve arrangement is in the second configuration, the first fluid flow path is closed and the second fluid flow path is open.

9. The system according to claim 8, wherein the fluid is saline.

10. The system according to claim 8, wherein the therapeutic agent is one of a non-steroidal anti-inflammatory agent, a steroid, an analgesic and an antimicrobial agent.

11. The system according to claim 8, wherein the impeller is magnetically coupled to the pump motor.

12. The system according to claim 8, wherein, when the valve arrangement is in the second configuration, the valve arrangement opens a fluid outlet lumen of the fluid chamber so that the therapeutic agent flows to the impeller.

13. The system according to claim 8, wherein, when the valve arrangement is in the second configuration, the valve arrangement closes a fluid supply lumen connecting the cassette to the external fluid source.

14. The system according to claim 8, wherein the valve arrangement includes at least one pincher valve.

15. The system according to claim 8, wherein the cassette includes a fluid storing reservoir and a level sensor outputting a signal corresponding to a level of fluid in the reservoir.

16. The system according to claim 15, wherein the console includes a controller determining a volume of fluid circulating through the cassette as a function of the signal.

* * * * *